United States Patent
Choi et al.

(10) Patent No.: US 11,324,458 B2
(45) Date of Patent: May 10, 2022

(54) ELECTRONIC DEVICE AND METHOD FOR CONTROLLING SAME

(71) Applicant: Samsung Electronics Co., Ltd., Suwon-si (KR)

(72) Inventors: Hyoung-seon Choi, Seoul (KR); Young-jae Oh, Suwon-si (KR); Min-hyoung Lee, Seongnam-si (KR); Seong-je Cho, Suwon-si (KR); Chul-ho Cho, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 407 days.

(21) Appl. No.: 16/343,254

(22) PCT Filed: Oct. 20, 2017

(86) PCT No.: PCT/KR2017/011678
§ 371 (c)(1),
(2) Date: Apr. 18, 2019

(87) PCT Pub. No.: WO2018/074894
PCT Pub. Date: Apr. 26, 2018

(65) Prior Publication Data
US 2019/0246991 A1      Aug. 15, 2019

(30) Foreign Application Priority Data
Oct. 20, 2016  (KR) .......................... 10-2016-0136537

(51) Int. Cl.
*A61B 5/145*      (2006.01)
*A61B 5/00*       (2006.01)
(Continued)

(52) U.S. Cl.
CPC ............ *A61B 5/7275* (2013.01); *A61B 5/002* (2013.01); *A61B 5/024* (2013.01); *A61B 5/0205* (2013.01);
(Continued)

(58) Field of Classification Search
CPC ............ A61B 5/14532; A61B 5/14503; A61B 2560/0223; A61B 5/0004; A61B 5/14514;
(Continued)

(56) References Cited

U.S. PATENT DOCUMENTS 8,114,350 B1 * 2/2012 Silver ................ A61B 5/14557
422/68.1
2008/0314395 A1   12/2008 Kovatchev et al.
(Continued)

FOREIGN PATENT DOCUMENTS

JP     2005-204787 A    8/2005
KR  10-2012-0043189 A   5/2012
(Continued)

*Primary Examiner* — Deborah L Malamud
(74) *Attorney, Agent, or Firm* — Jefferson IP Law, LLP

(57) ABSTRACT

Provided are an electronic device and a method for controlling the same. An electronic device for providing continuous blood glucose monitoring comprises: a first sensor for measuring a glucose level of an interstitial fluid in order to predict blood glucose; a second sensor disposed on an inner surface of the electronic device to be in contact with a human body, in order to measure at least one of a blood flow and a heart rate of the human body; and a processor for determining a diffusion time during which glucose present in blood diffuses into the interstitial fluid, on the basis of characteristics of a signal generated by the second sensor, and predicting the blood glucose on the basis of the glucose level measured by the first sensor and the determined diffusion time.

13 Claims, 16 Drawing Sheets

(51) Int. Cl.
- *A61B 5/026* (2006.01)
- *A61B 5/024* (2006.01)
- *A61B 5/0245* (2006.01)
- *A61B 5/1495* (2006.01)
- *A61B 5/0205* (2006.01)
- *A61B 5/1486* (2006.01)
- *A61B 5/1473* (2006.01)
- *A61M 5/142* (2006.01)

(52) U.S. Cl.
CPC ............ *A61B 5/026* (2013.01); *A61B 5/0245* (2013.01); *A61B 5/0261* (2013.01); *A61B 5/02416* (2013.01); *A61B 5/145* (2013.01); *A61B 5/1473* (2013.01); *A61B 5/1486* (2013.01); *A61B 5/1495* (2013.01); *A61B 5/14532* (2013.01); *A61B 5/4839* (2013.01); *A61B 5/4848* (2013.01); *A61B 5/6824* (2013.01); *A61B 5/6886* (2013.01); *A61M 5/142* (2013.01); *A61B 5/7225* (2013.01)

(58) Field of Classification Search
CPC ........... A61B 5/0031; A61B 5/72; A61B 5/05; A61B 5/14; A61B 5/145; A61B 5/1451; A61B 5/7282; A61B 2562/227; A61B 5/157; A61B 5/318; A61B 5/486; A61B 5/024; A61B 2562/00; A61B 5/00; A61B 5/02; A61B 5/0245; A61B 5/026; A61N 1/05
See application file for complete search history.

(56) References Cited

U.S. PATENT DOCUMENTS

| | | |
|---|---|---|
| 2011/0077490 A1 | 3/2011 | Simpson et al. |
| 2013/0060098 A1 | 3/2013 | Thomsen et al. |
| 2016/0007890 A1 | 1/2016 | Kovatchev et al. |
| 2016/0157733 A1 | 6/2016 | Gil |

FOREIGN PATENT DOCUMENTS

| | | |
|---|---|---|
| KR | 10-1145668 B1 | 5/2012 |
| KR | 10-1512076 B1 | 4/2015 |
| KR | 10-1637325 B1 | 7/2016 |
| WO | 2016/102227 A1 | 6/2016 |

* cited by examiner (a)          (b)          (c)

ELECTRONIC DEVICE AND METHOD FOR CONTROLLING SAME

FIELD

This disclosure relates to an electronic device and a method for controlling the same. More specifically, the disclosure relates to an electronic device for providing real-time blood glucose information by improving a blood glucose prediction error based on blood flow and heart rate information of a user sensed through a sensor, and a method for controlling the same.

DESCRIPTION OF THE RELATED ART

A continuous glucose monitoring system (CGMS) is a system for continuously measuring blood glucose and providing measured blood glucose on a real time basis, even if a patient with hypoglycemia or hyperglycemia does not visit a medical staff.

However, most of continuous glucose sensors (CGS) used in CGMS measure blood glucose (BG) by sampling interstitial fluid glucose (IG) of interstitial fluid. Therefore, the method of predicting the blood glucose by the glucose sensor is, when the glucose included in the blood (BG) diffuses into the glucose in interstitial fluid (IG), measuring by the glucose sensor the IG level of the interstitial fluid and predicting the BG in the blood. Therefore, the level of blood glucose predicted by the CGMS is not from measuring the blood glucose of actual blood vessels and thus, an error of blood glucose measurement due to a time delay caused by the diffusion of glucose from the blood into the interstitial fluid is generated.

However, in the case of a patient with the hypoglycemia, the blood glucose falls within a short period of time and the patient may be in a light-threatening situation. Therefore, there is a need for a technology for developing the CGMS which minimizes the time delay between the glucose level of the blood vessel and the glucose level of the interstitial fluid, in order to predict and provide accurate blood glucose.

Also, with the development of ubiquitous technology, real-time monitored blood glucose information may be shared with medical staff and emergency centers. Therefore, there is a need for various technologies which may provide the CGMS optimized for a patient with the hypoglycemia and a patient with the hyperglycemia based on the accurate blood glucose measurement result, and enable remote diagnosis and prescription by a medical institution.

DETAILED DESCRIPTION

Technical Problem

The disclosure is to solve the above problems and is purposed to provide an electronic device for providing accurate blood glucose measurement on a real-time basis by reducing a time delay for blood glucose prediction using a sensor for measuring blood flow and heart rate, and a method for controlling the same.

Technical Solution

According to an embodiment of the disclosure, an electronic device for providing continuous blood glucose monitoring includes a first sensor for measuring a glucose level of an interstitial fluid in order to predict blood glucose, a second sensor disposed on an inner surface of the electronic device to be in contact with a human body, in order to measure at least one of a blood flow and a heart rate of the human body, and a processor for determining a diffusion time during which glucose present in blood diffuses into the interstitial fluid, on the basis of characteristics of a signal generated by the second sensor, and predicting the blood glucose on the basis of the glucose level measured by the first sensor and the determined diffusion time.

According to an embodiment of the disclosure, a method for providing continuous blood glucose monitoring by an electronic device includes measuring a glucose concentration of an interstitial fluid in order to predict blood glucose by a first sensor; measuring at least one of a blood flow and a heart rate of a human body by a second sensor disposed on an inner surface of the electronic device to be in contact with the human body; determining a diffusion time during which glucose present in blood diffuses into the interstitial fluid, on the base of characteristics of a signal generated by the second sensor; and predicting the blood glucose on the basis of the glucose concentration measured by the first sensor and the determined diffusion time.

As described above, according to various embodiments of the disclosure, the electronic device may provide a user with accurate blood glucose information by reducing time delay between glucose in blood and measurement of glucose in interstitial fluid.

DETAILED DESCRIPTION OF EXEMPLARY EMBODIMENTS

Figure 1:
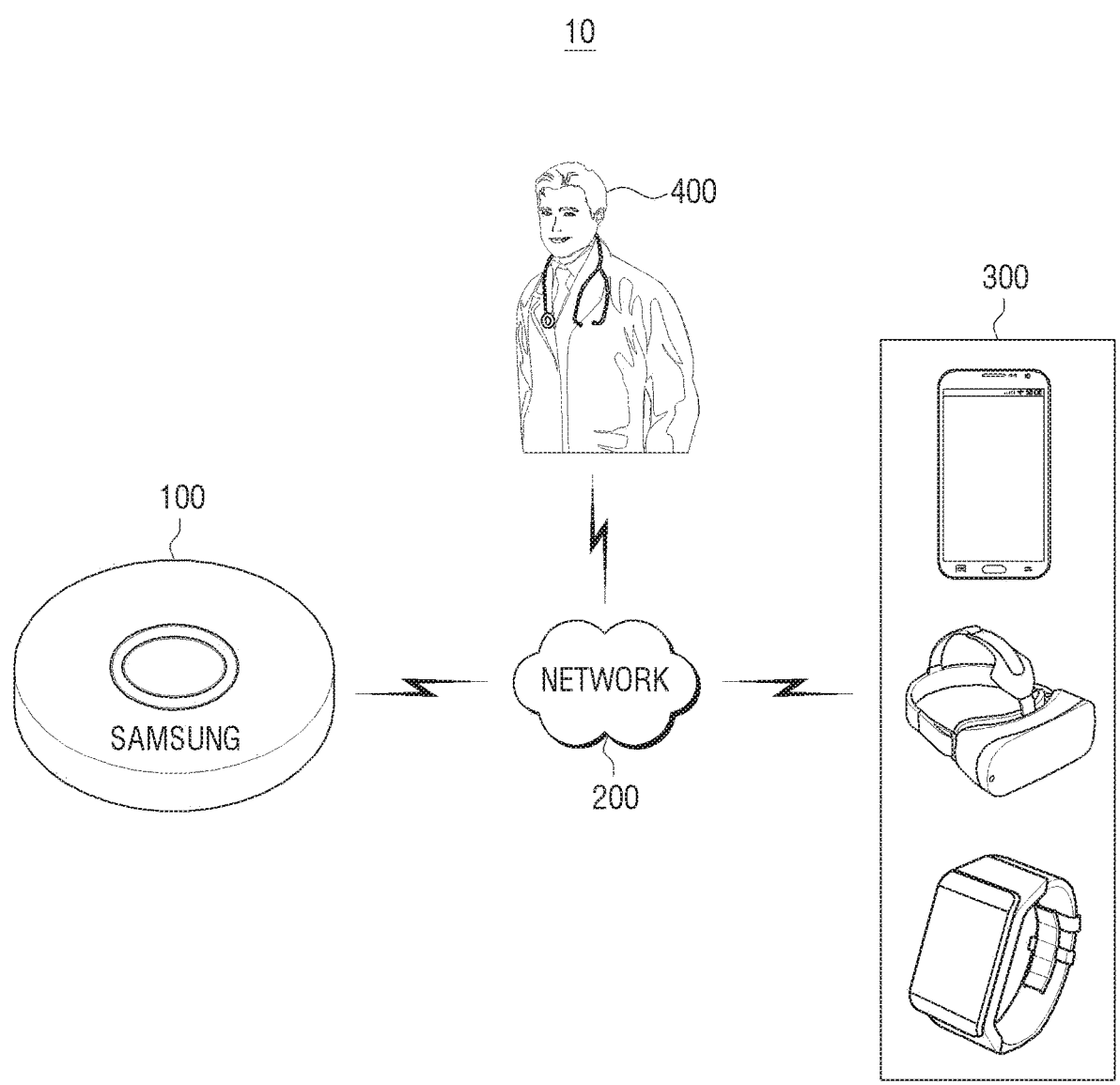
FIG. 1 is a view illustrating a continuous blood glucose monitoring according to an embodiment.

Hereinafter, embodiments according to the disclosure will be described in detail with reference to the contents described in the accompanying drawings. In addition, a method of manufacturing and using the embodiment will be described in detail with reference to the description of the attached drawings. Like reference numbers or designations in the various drawings indicate components or configurations that perform substantially the same function.

The terms such as first and second, and the like may be used to describe a variety of elements, but the elements should not be limited by these terms. The terms are used only for the purpose of distinguishing one element from another.

The term "and/or" includes a combination of a plurality of elements or one of the plurality of elements.

The terms used in the disclosure are provided to describe particular embodiments only, and are not intended to limit and/or the embodiment. A singular expression, unless the context clearly used otherwise, includes plural meaning.

In the disclosure, it is to be understood that the terms such as "comprise" or "consist of" are used herein to designate a presence of a characteristic, number, step, operation, element, component, or a combination thereof, and not to preclude a presence or a possibility of adding one or more of other characteristics, numbers, steps, operations, elements, components or a combination thereof. For the reference numeral on each drawing indicates the component which performs substantially the same function.

FIG. 1 is a view illustrating a continuous blood glucose monitoring according to an embodiment.

Referring to FIG. 1, in a system 10, the electronic device 100 may communicate with various external electronic devices 300, and a medical institution 400 through a network 200.

In FIG. 1, the electronic device 100 may represent a first electronic device, and at least one of the various external electronic devices 300 may represent a second electronic device.

The first electronic device 100 may predict blood glucose by measuring glucose of the interstitial fluid through a first sensor. For example, the first sensor may be a glucose sensor which is capable of measuring a glucose level in the continuous glucose monitoring system (CGMS). The first electronic device 100 according to an embodiment of the disclosure may include a second sensor capable of measuring blood flow and/or heart rate. For example, the second sensor may be a photoplethysmography (PPG) sensor, but is not limited thereto. The first electronic device 100 is able to predict the blood glucose based on the data measured by the sensors, and provide a user with a notification related to hypoglycemia or hyperglycemia. When the first electronic device 100 includes a display and/or a speaker, or the like, the first electronic device 100 may provide a user with a notification related to hypoglycemia or hyperglycemia through various user interfaces (UIs) and/or sounds.

The first electronic device 100 may provide the predicted blood glucose data to the second electronic device 300 and/or an emergency rescue center such as the medical institution 400, via the wired and/or wireless network 200. The second electronic device 300 may provide a user with a notification related to hypoglycemia or hyperglycemia based on the predicted blood glucose information received from the electronic device 100.

The second electronic device 300 may be various electronic devices such as a smartphone, a tablet PC, a smart watch, a head-mounted display, a smart watch, a smart band, a smart ring, a smart glasses, or the like, but is not limited thereto.

The medical institution 400 may provide the remote diagnosis and remote prescription to the patient based on the blood glucose information provided from the first electronic device 100. The medical institution 400 may be an external server. In addition, the medical institution 400 may be an emergency rescue center (for example, the 911 Center). The medical institution 400 may provide appropriate medical support to critical hypoglycemic and/or hyperglycemic patients. For example, if the blood glucose and heart rate information provided by the first electronic device 100 is included within a range of unconsciousness of a patient, the medical institution 400 may provide appropriate medical support to the patient. In addition, the second electronic device 300 may check the status of the patient on a real-time basis based on the information provided by the first electronic device 100.

Also, according to another embodiment, the first electronic device 100 may be configured to include the first sensor to measure glucose of interstitial fluid through the first sensor, and the second electronic device 300 may be configured to include the second sensor to measure the blood flow and/or heart rate of the user on a real-time basis through the second sensor. Also, the implementation is changeable such that the first sensor may be included in the second electronic device 300, and the second sensor may be included in the first electronic device 100.

The first electronic device 100 may receive the heart rate sensing data measured from the second electronic device 300 including the second sensor through the network 200. The first electronic device 100 may predict the blood glucose based on the heart rate sensing data received from the second electronic device 300, and transmit the predicted glucose information to the second electronic device 300 through the network. The second electronic device 300 may provide the user of the first electronic device 100 with a notification related to hypoglycemia or hyperglycemia based on the blood glucose information received from the first electronic device 100.

For example, the first electronic device 100 may be the continuous glucose monitoring (CGM) device including the first sensor. The second electronic device 300 may be various wearable devices including the second sensor. The second sensor may be configured to be disposed inside the wearable device 300 such as the smart watch and to be in contact with the human body. The second electronic device 300 may transmit the data information sensed from the second sensor to the first electronic device 100 which is the CGM device.

The first electronic device 100 may transmit blood glucose information predicted based on the heart rate sensing data received from the second electronic device 300 to the second electronic device 300. The second electronic device 300 may provide the user with notification related to hypoglycemia or hyperglycemia based on the blood glucose information received from the first electronic device 100.

According to another embodiment, the first electronic device 100 which is configured to include the first sensor may measure the glucose of interstitial fluid through the first sensor and transmit the measured data to a server (not shown). The second electronic device 300 which is configured to include the second sensor may measure blood flow and/or heart rate of the user through the second sensor on a real-time basis and transmit the measured data to a server (not shown). The server may be included in the first electronic device 100 or the second electronic device 300, or present in the outside, instead of the first electronic device 100 and the second electronic device 300. The external server may determine hypoglycemia or hyperglycemia of the user based on the information received from the first electronic device 100 and the second electronic device 300, and provide the related information to at least one of the first electronic device 100, the second electronic device 300, and/or the medical institution 400. The first electronic device 100, the second electronic device 300, and/or the medical institution 400 may provide the user with a notification related to hyperglycemia or hypoglycemia in various ways based on the information related to the blood glucose provided from the server.

The first electronic device 100 and the second electronic device 300, when including configurations such as a speaker, a display, a vibrator, or the like, capable of providing a notification related to blood glucose, may provide the user with the notification related to the blood glucose in various ways. The embodiments above are merely exemplary for describing the disclosure but are not limited thereto.

Figure 2:
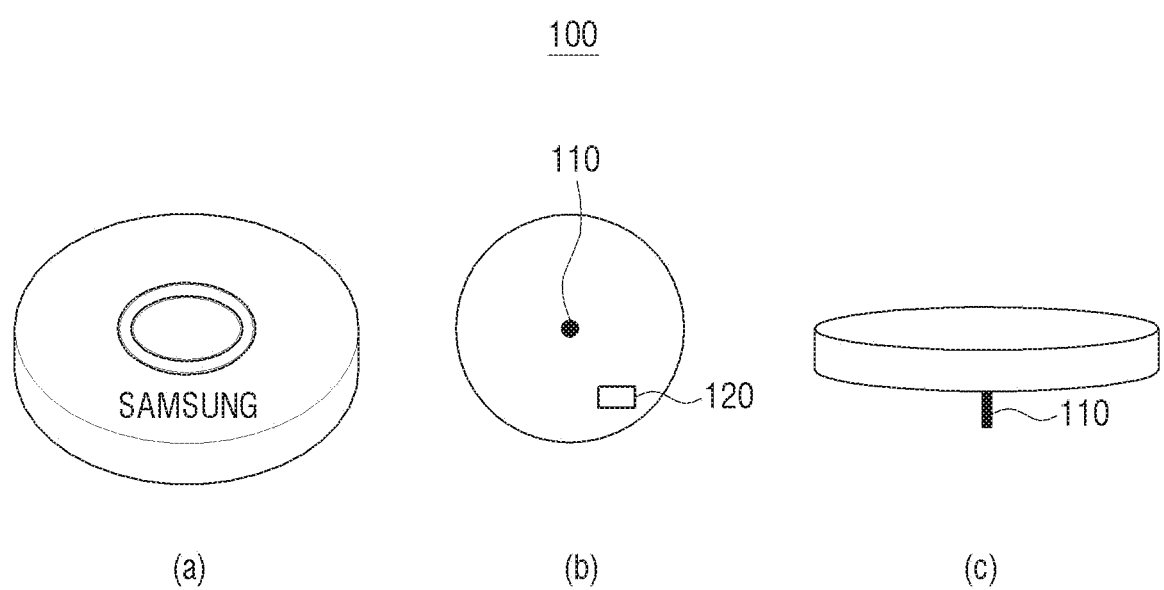
FIG. 2 is a view illustrating sectional views of the electronic device according to an embodiment.

The electronic device 100 will be described in greater detail below with respect to FIG. 2. Referring to FIG. 2, for convenience of description, a configuration and a method for controlling of the electronic device 100 including both the first sensor and the second sensor is described but is not limited thereto.

FIG. 2 is a view illustrating sectional views of the electronic device according to an embodiment.

FIG. 2A illustrates a cross-sectional view that is seen from the top of the electronic device 100. The electronic device 100 may include a display and/or an inputter for receiving a user command.

FIG. 2B is a sectional view in which the electronic device 100 is viewed from the bottom, and FIG. 2C is a view illustrating a side of the electronic device 100.

The electronic device 100 may include the first sensor 110 capable of measuring glucose of interstitial fluid. The first sensor 110 may be inserted into the skin. The first sensor 110 may be configured in a form of a needle capable of measuring the glucose of interstitial fluid electrochemically, but is not limited thereto. The first sensor 110 may be various sensors commonly used in electronic devices that provide the CGM.

According to one embodiment of the disclosure, the electronic device 100 may include the second sensor 120 disposed on an inner surface of the electronic device 100 to be in contact with a human body. The second sensor 120 may measure blood flow and/or heart rate of a human body. The second sensor 120 may be composed of at least one light emitting diode (LED) and a photo diode (PD). The second sensor 120 may irradiate the skin with LED and recognize the PD that is reflected from the skin.

For example, the second sensor 120 may be a photoplethysmography (PPG) sensor, but is not limited thereto, and may be implemented as various sensors such as an electrocardiogram capable of measuring the heart rate. In the disclosure, for convenience of description, the second sensor 120 will be described as the PPG sensor as an example.

The electronic device 100 may be implemented in an enlarged manner by further including sensors other than the first sensor 110 and the second sensor 120. For example, various sensors such as a heating sensor and a respiration sensing sensor, or the like may be included.

Figure 3:
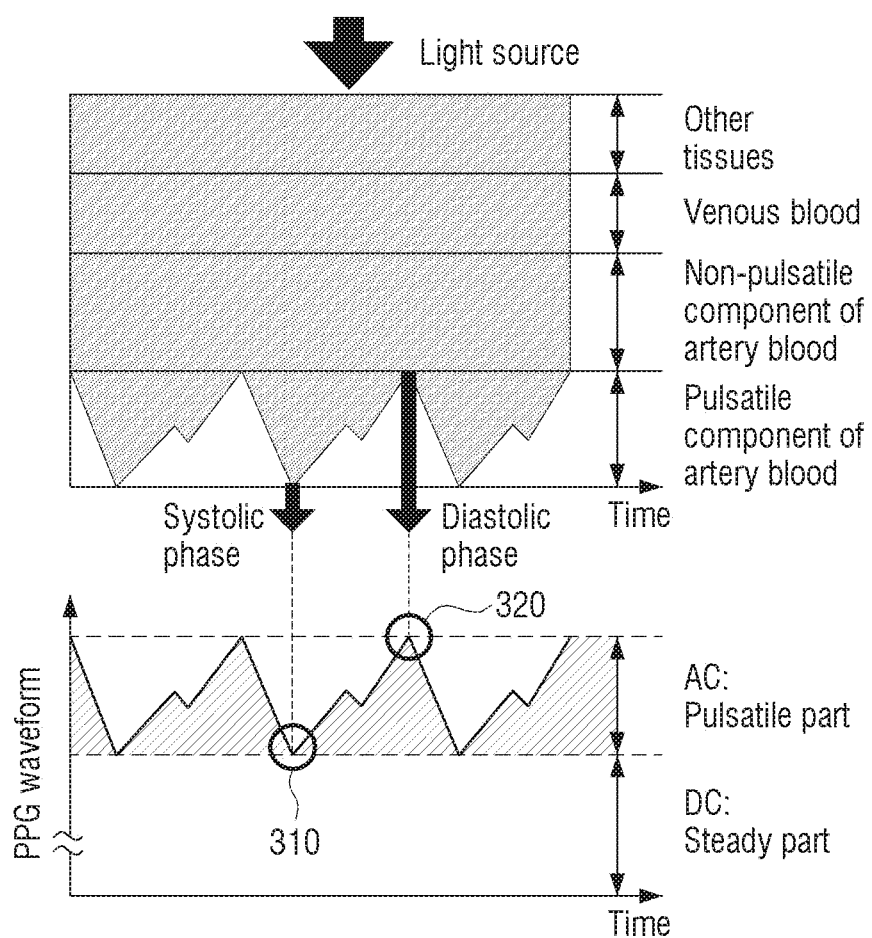
FIG. 3 is a view to describe a photoplethysmography (PPG) sensor.

FIG. 3 is a view to describe a photoplethysmography (PPG) sensor.

Referring to FIG. 3, the PPG signal may be divided into an AC portion where a signal change is present and a DC portion where a signal change is not present according to time.

In the AC portion, a low signal portion 310 is a point of time when the heart is contracted, and a high signal portion 320 is the point of time when the heart is relaxed. Thus, based on the PPG signal, heart rate according to contraction and relaxation of the heart may be determined. Further, the area of the AC portion (shaded portion) may be proportional to the volume of the blood vessel. Therefore, when the area of the AC portion is smaller than the other time within the same time, it may be seen that the blood vessel is in a contracted state.

The DC portion may become smaller as the ratio of the AC portion gets higher. Accordingly, the electronic device 100 may determine the blood flow and/or the heart rate according to the size of the DC value. For example, when the DC value is low, the blood flow amount may be high. Also, high blood flow amount may indicate that the blood amount increases in a predetermined time, and thus mean that the heart rate is increased. In other words, the IG in the blood can rapidly diffuse into interstitial fluids when the heart rate is fast.

According to one embodiment, when the PPG sensor is used for the electronic devices which provide the CGM, the electronic device 100 may be implemented to advance the time for measuring glucose of interstitial fluid according to the heart rate determined based on a signal generated from the PPG sensor. According to an embodiment, the electronic device 100 may measure blood glucose which is close to the actual blood glucose by measuring the glucose of interstitial fluid for the time corresponding to the PPG signal. Therefore, the electronic device 100 may reduce the blood glucose measurement errors according to time delay which is generated as the glucose in blood diffuses into the interstitial fluid.

Figure 4A:
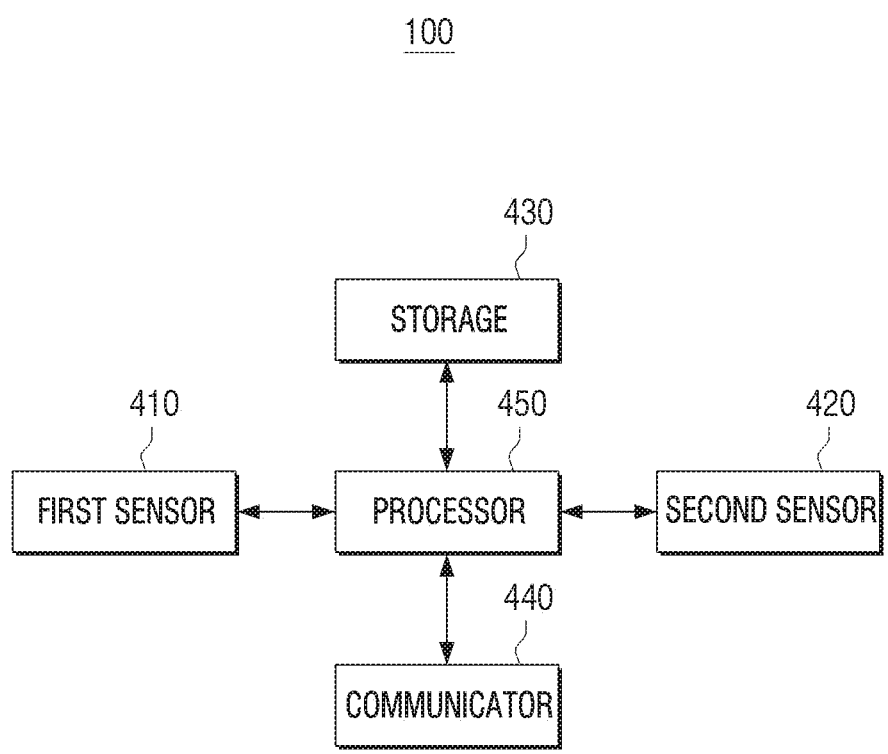
FIGS. 4A, 4B and 4C are simple block diagrams constituting the continuous blood glucose monitoring system according to an embodiment.
Figure 4B:
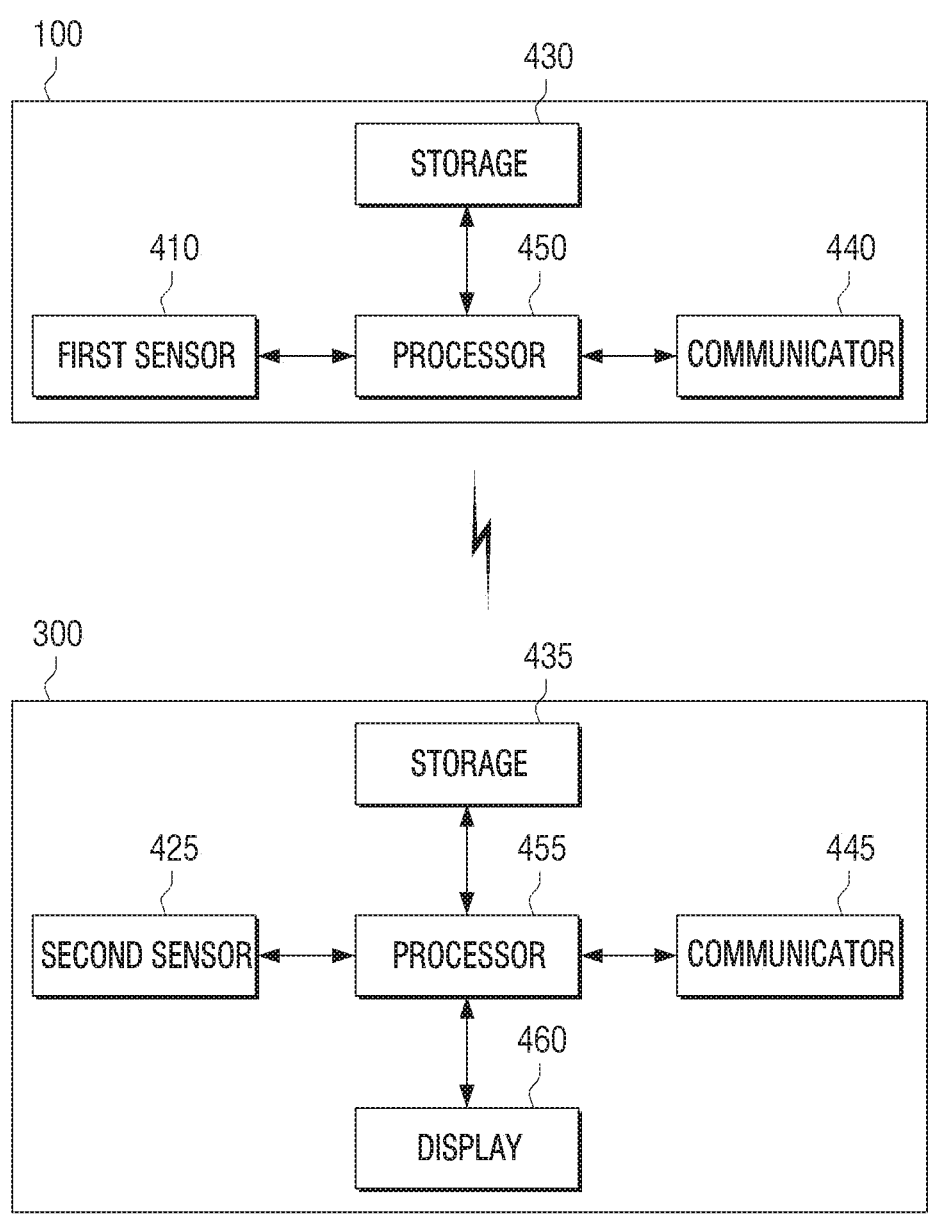
Figure 4C:
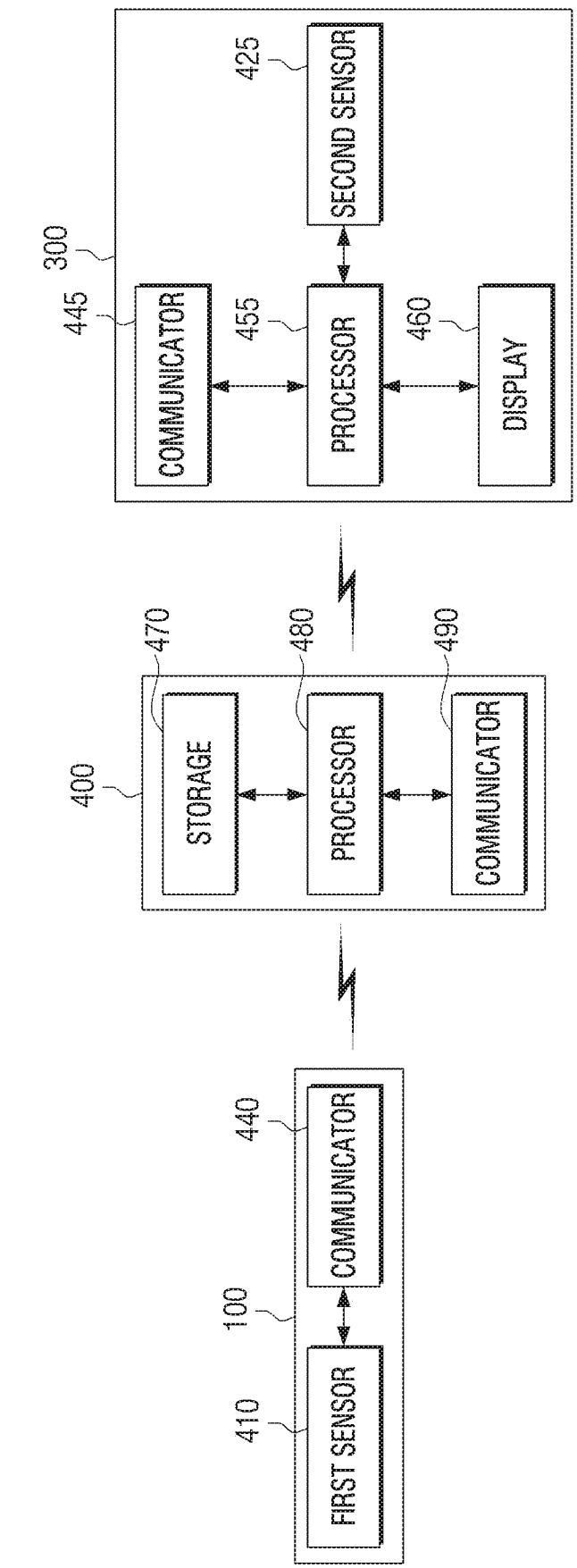

FIGS. 4A to 4C are simple block diagrams constituting the continuous blood glucose monitoring system according to an embodiment. The configurations constituting the system and the electronic device of FIGS. 4A to 4C may be implemented by deleting configurations or adding configurations which have not been illustrated.

FIG. 4A is a simple block diagram constituting the electronic device including the first sensor and the second sensor according to an embodiment.

Referring to FIG. 4, the electronic device 100 may include a first sensor 410, a second sensor 420, a storage 430, a communicator 440, and a processor 450. According to an embodiment, the first sensor 410 may be a general glucose sensor which measures the glucose of interstitial fluid to predict the blood glucose by the device which provides the CGM.

As described in FIG. 2, the first sensor 410 according to an embodiment may be the glucose sensor in a form of a needle that may measure the blood glucose in the interstitial fluid by an electrochemical reaction. In addition, the first sensor 410 may be disposed at a bottom side of the electronic device 100 and inserted into the skin. However, this is merely exemplary for describing the disclosure, and the first sensor 410 may be the glucose sensors in various forms that may measure the glucose of interstitial fluid.

The second sensor 420 may be a heart rate measurement sensor including the LED and the PD. The second sensor 420 may be disposed on an inner surface of the bottom side of the electronic device 100 to be in contact with the skin of the human body. The second sensor 420 may irradiate light onto the skin and generate a signal according to the change of the light absorption. For example, the second sensor 420 may be a photoplethysmography sensor that is capable of measuring the blood flow and/or heart rate of the human body, but is not limited thereto.

The storage 430 may store data measured by the first sensor 410 and the second sensor 420. In addition, the storage 430 may store a blood glucose level according to symptoms by levels of hypoglycemia and hyperglycemia.

The storage 430 may store a prescription of a patient which may be provided by levels of hypoglycemia and hyperglycemia, recommended food information, and data such as insulin infusion cycle, an insulin infusion amount, and the like. The above examples are merely exemplary, and the storage 430 may receive various information related to blood glucose through an external server in real time and store the same, or store information received from the user.

The communicator 440 may enable the electronic device 100 to communicate with an external device (for example: an external server, another electronic device, or the like). The communicator 440 may be connected to the network through wireless communication or wired communication and communicate with the external device.

The wireless communication may include at least one of wireless fidelity (Wi-Fi), Bluetooth (BT), near field communication (NFC), global positioning system (GPS), or cellular communication (for example: long term evolution (LTE), long term evolution-advanced (LTE-A), code division multiple access (CDMA), wideband code division multiple access (WCDMA), universal mobile telecommunications system (UMTS), wireless broadband internet (Wibro) or global system for mobile communications (GSM), etc.). The wired communication may include at least one of a universal serial bus (USB), a high definition multimedia interface (HDMI), a recommended standard 232 (RS-232) or a plain old telephone service (POTS).

The communicator 440 may receive position information of the electronic device 100 through communication module such as a global positioning system (GPS), Bluetooth low energy (BLE), near field communication (NFC), or the like.

The electronic device 100 may further include a memory (not shown). The memory may store a program for operating the processor 450.

The memory may be implemented as a non-volatile memory, a volatile memory, a flash memory, a hard disk drive (HDD), or a solid state drive (SSD), or the like. The memory may be accessed by the processor 450 and reading/recording/correcting/updating, or the like of data by the processor 450 may be performed. The memory include at least one type of storage medium such as read-only memory (ROM), random-access memory (RAM), electrically erasable and programmable ROM (EEPROM), programmable read-only memory (PROM), magnetic memory, and magnetic disk.

The processor 450, based on the characteristics of the signal generated by the second sensor 420, may determine diffusion time during which the glucose present in the blood diffuses into the interstitial fluid and predict the blood glucose based on the glucose level measured by the first sensor 410 and the diffusion time determined by the second sensor 420.

When the height of the amplitude of the signal in the portion (AC portion) where the change of a signal generated by the second sensor 420 is present becomes periodically less than or equal to the designated value, the processor 450 may determine that the blood flow and/or the heart rate is out of the normal range, and determine the diffusion time during which the glucose diffuses into the interstitial fluid to be proportional to the blood flow and/or the heart rate.

When a peak-to-peak interval of the signal generated by the second sensor 420 is equal to or less than a designated value, the processor 450 may determine that the blood flow and/or heart rate is out of the normal range, and determine the diffusion time during which the glucose diffuses into the interstitial fluid to be proportional to the blood flow and/or the heart rate.

When the size of the DC value of the portion (DC portion) in which the change of the signal generated by the second sensor 420 is not present is equal to or less than a designated value, the processor 450 may determine that the blood flow and/or heart rate is out of the normal range, and determine the diffusion time during which the glucose diffuses into the interstitial fluid to be proportional to the blood flow and/or the heart rate.

The processor 450 may determine whether the first sensor 410 is inserted into the human body according to the signal generated by the PD of the second sensor 420.

When the signal generated by the PD has a variable value at a threshold value or over, the processor 450 may determine that the first sensor 410 is not inserted to the human body and provide a connection failure warning to the user.

When the heart rate and blood flow amount measured by the signal generated by the second sensor 420 are equal to or greater than a designated value, the processor 450 may control the first sensor to advance the hypoglycemia prediction time by setting a slope value at a point at which the glucose level measured by the second sensor becomes a designated value or less to be greater than or equal to a threshold value.

The processor 450 may predict the glucose level to be measured based on the glucose concentration level measured by the first sensor 410 on a time basis and provide the notification of hypoglycemia to the user before the time when the predicted glucose level is less than or equal to a designated value.

When the blood flow and the heart rate measured by the second sensor 420 is greater than or equal to a threshold value, and the glucose level measured by the first sensor 410 is within a designated range, the processor 450 may provide the notification of hypoglycemia.

The electronic device 100 may further include an insulin pump (not shown), and when the predicted blood glucose is hyperglycemia, the processor 450 may determine the insulin infusion cycle differently by times based on the blood flow and the heart rate measured by the second sensor 420.

FIG. 4B is a simple block diagram of the first electronic device including the first sensor and the second electronic device including the second sensor, according to another embodiment.

Referring to FIG. 4B, a system 10 includes the first electronic device 100 and the second electronic device 300.

The first electronic device 100 may include the first sensor 410, the storage 430, the communicator 440, and the processor 450, and the second electronic device 300 may include a second sensor 425, a storage 435, a communicator 445, a processor 455, and a display 460.

The first sensor 410, the storage 430, the communicator 440, and the processor 450 constituting the first electronic device 100 may be the same as the remaining configurations other than the second sensor 420, among the configurations of the electronic device 100 as described in FIG. 4A.

The communicator 440 may receive heart rate information data sensed through the second sensor 425 of the second electronic device 300.

The processor 450, based on the characteristic of the signal generated by the second sensor 420 received through the communicator 440, may determine the diffusion time during which the glucose present in the blood diffuses into the interstitial fluid, and predict blood glucose based on the glucose level measured by the first sensor 410 and the diffusion time determined by the second sensor 425.

The processor 450 may transmit the predicted blood glucose information to the second electronic device 300 through the communicator 440.

The second sensor 425, the storage 430, the communicator 440, and the processor 455 constituting the second electronic device 300 may be the same as the configurations corresponding to the second sensor 420 among the configurations of the electronic device 100 as illustrated in FIG. 4A.

The processor 455 may receive the blood glucose information predicted through the processor 450 from the first electronic device 100 through the communicator 445, and provide a user with a notification related to hypoglycemia or hyperglycemia based on the received blood glucose information.

The processor 455 may control the display 460 to display the notification related to hypoglycemia or hyperglycemia on the display 460 through various UIs.

The display 460 may be various types of displays such as a flexible display, a display including a touch screen, or the like.

FIG. 4C is a simple block diagram of a system for analyzing continuous blood glucose monitoring through a server according to still another embodiment.

Referring to FIG. 4C, the system 10 includes the first electronic device 100, the second electronic device 300, and a server 400.

The first electronic device 100 may include the first sensor 410 and the communicator 440. The first sensor 410 and the communicator 440 may have the same configurations corresponding to the first sensor 410 and the communicator 440 among the configurations of FIG. 4A.

The blood glucose information data sensed through the first sensor 410 may be transmitted to the server 400 through the communicator 440.

The second electronic device 100 may include the second sensor 425, the communicator 445, and the processor 455. The second sensor 425 and the communicator 445 may have the same configuration corresponding to the second sensor 420 among the configurations of FIG. 4A.

The heart rate information sensed by the second sensor 425 may be transmitted to the server 400 through the communicator 445. The processor 455 may control the display 460 to display the notification related to hypoglycemia or hyperglycemia on the display 460 through various UIs based on the blood glucose information received from the server 400.

The server 400 may include a storage 470, a processor 480, and a communicator 490. The storage 470 and the communicator 490 may be the same as the configurations of the storage 430 and the communicator 440 of FIG. 4A.

The storage 470 may store the blood glucose data information sensed by the first sensor 410 received from the first electronic device 100. The storage 470 may store the heart rate data information sensed from the second sensor 425 received from the second electronic device 300. The storage 470 may store various data stored in the storage 430 illustrated in FIG. 4A.

The processor 480 may predict the blood glucose level of interstitial fluid and the blood glucose level diffusion time of interstitial fluid based on the blood glucose information received from the first electronic device 100 and the heart rate information received from the second electronic device 300, and store the predicted information in the storage 470.

The processor 480 may have the same configuration as the processor 450 described in FIG. 4A. The processor 480 may transmit the blood glucose information determined based on the sensed values received from the first electronic device 100 and the second electronic device 300 to the first electronic device 100 and the second electronic device 300. The first electronic device 100 and the second electronic device 300 may provide a notification of hypoglycemia or hyperglycemia to the user in various ways based on the blood glucose information received from the server 400. For example, the second electronic device 300 may display a notification of hypoglycemia in different colors for each blood glucose level through the display 460.

However, the above examples are merely exemplary to describe the disclosure, and the block diagram constituting the first electronic device 100, the second electronic device 300, and the server 400, and the functions thereof may be changed from each other, the block diagram may be deleted, and a block diagram having a new function may be added.

Figure 5:
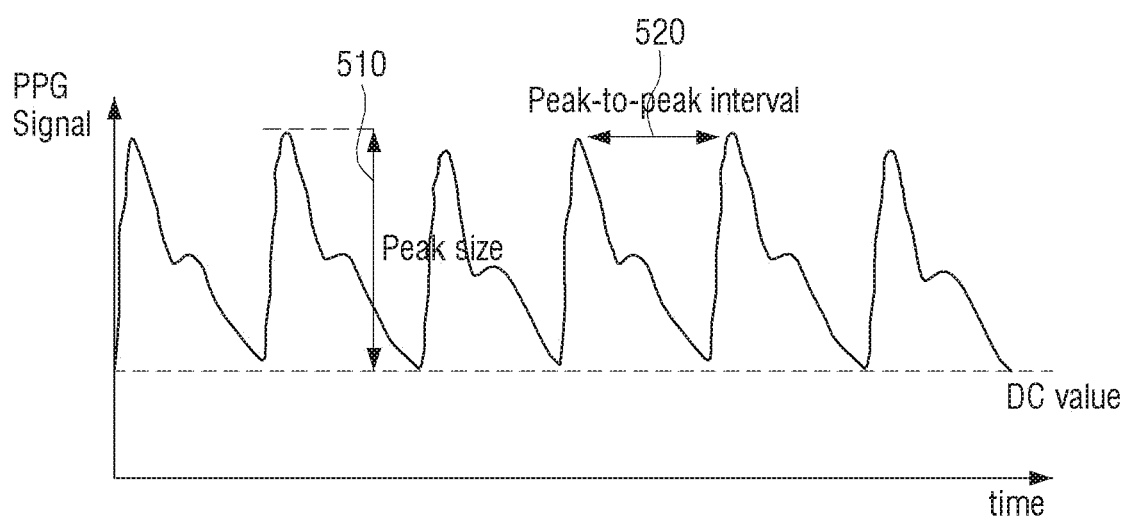
FIG. 5 is a view illustrating an output signal of the PPG sensor according to an embodiment.

FIG. 5 is a view illustrating an output signal of the PPG sensor according to an embodiment.

As illustrated in FIG. 5, the PPG sensor may output a PPG signal which is generated, as light which is irradiated to the skin is absorbed by the glucose of the interstitial fluid.

The PPG signal may have an amplitude 510 having different heights according to blood flow amount. In addition, the PPG signal may periodically have a peak-to-peak interval 520 where the peak is the highest value among the signals. The PPG signal may have a DC value in which there is no signal change amount.

The blood glucose in blood may be predicted based on the PPG signal generated by the PPG sensor.

For example, when the blood flow is high in the blood vessel, it means that the amount of blood passing through the blood vessel is large. If the amount of blood in the blood vessel is large, the amount of light absorbed by the blood among the light irradiated to the skin increases. Therefore, the amount of light which is reflected from the blood detected by the PD of the PPG sensor decreases. In contrast, when the blood flow in the blood vessel is low, the amount of blood passing through the blood vessel is small and thus, the amount of reflected light in the light irradiated to the skin increases. Therefore, the amplitude of the PPG signal may have a different value in accordance with the amount of light reflected from the blood.

That is, if the blood flow is high, the amplitude 510 may be high, and if the blood flow is low, the amplitude 510 may be low. In addition, when the heart rate is rapid, the peak-to-peak interval 520 may be narrow, and when the heart rate is slow, the peak-to-peak interval 520 may be wider. The heart rate and the blood flow may have a proportional relationship to each other. For example, when the heart rate is rapid, the blood flow passing through the blood vessel during the same time may increase. Therefore, large blood flow may mean rapid heart rate.

The electronic device 100, according to one embodiment of the disclosure, may determine the diffusion time during which the glucose present in the blood diffuses into the interstitial fluid, based on the characteristics (for example, amplitude, peak-to-peak distance, the DC value, or the like) of the signal generated by the PPG sensor. In addition, the electronic device 100 may predict the blood glucose based on the glucose level measured by the glucose sensor for measuring the glucose level of the interstitial fluid and the diffusion time determined by the PPG sensor.

When the height of the amplitude 510 of the signal of the portion (AC portion) in which a change of the signal generated by the PPG sensor is present becomes less than or equal to a designated value periodically, the electronic device 100 may determine that the blood flow and/or the heart rate is out of the normal range, and determine the diffusion time during which the glucose diffuses into the interstitial fluid to be proportional to blood flow and/or heart rate.

For example, when the blood flow has a value which is greater than or equal to the designated first range or the heart rate has a value which is greater than or equal to the designated first range, the electronic device 100 may determine that the blood flow and the heart rate of the user is out of the normal range, and control so that the diffusion time during which glucose diffuses into the interstitial fluid to be proportional to the time of measuring heart rate by the PPG signal.

For example, if the blood flow and heart rate are within the normal range, it may be assumed that the time during which the glucose sensor (first sensor) measures the glucose of the interstitial fluid is the first time cycle during which the glucose diffuses from the blood into the interstitial fluid. At this time, when the heart rate is out of the normal range measured by the PPG sensor, the electronic device 100 may control the glucose sensor so that the glucose sensor (second sensor) measures the glucose of the interstitial fluid at a time when the PPG sensor detects abnormal heart rate, which is the time earlier than the first time cycle.

The electronic device 100, when the peak-to-peak interval of the signal generated by the PPG sensor is less than or equal to a designated value, may determine that the blood flow and/or the heart rate is out of the normal range, and determine the diffusion time during which the glucose diffuses into the interstitial fluid to be proportional to the blood flow and/or the heart rate.

For example, the peak-to-peak interval of the PPG signal may become narrow if the heart contraction and relaxation is repeated rapidly. Therefore, if the peak-to-peak interval of the PPG signal is lower than the first range, which is the normal heart rate range, the electronic device 100 may determine that the blood flow and/or heart rate of the user is out of the normal range. Accordingly, the electronic device 100 may control the glucose sensor to measure the glucose in the interstitial fluid at a time when the PPG sensor detects abnormal heart rate, which is a time earlier than the time cycle in which the glucose sensor (first sensor) measures the glucose of the interstitial fluid in the normal heart rate range.

In addition, in the DC portion where there is no PPG signal change may be in inverse proportion to the area of the AC portion. Therefore, the blood flow may be predicted based on the DC value of the PPG signal.

According to an embodiment, the electronic device 100, when the size of the DC value in the portion (DC portion) in which there is no change of the signal generated by the PPG sensor is greater than or equal to a designated value, may determine that the blood flow and/or the heart rate is out of the normal range, and determine that the diffusion time during which the glucose diffuses into the interstitial fluid to be proportional to the blood flow and/or heart rate.

For example, if the blood flow and/or heart rate of the blood vessel is high, the PPG signal amplitude 510 in the AC portion may be low and the peak-to-peak interval 520 may be narrow. Therefore, the area of the AC portion may be small and the area of the DC portion may be large. Thus, the DC value may be a value in the first range, when the blood flow and heart rate are in a normal range. When the DC value of the signal generated by the PPG sensor is equal to or greater than the first value, the electronic device 100 may determine that the blood flow and the heart rate are out of the normal range, and control the glucose sensor so that the glucose sensor (first sensor) measures the glucose of the interstitial fluid at the time when the PPG sensor detects abnormal heart rate which is the time earlier than the time cycle in which the glucose sensor (first sensor) measures glucose of the interstitial fluid in the normal heart rate range.

By the method above, the electronic device 100 may reduce the blood glucose error which may occur due to time delay of diffusion of the glucose in the blood into interstitial fluid by controlling the measuring time of the glucose of the interstitial fluids according to the blood flow and/or heart rate.

FIGS. 6 and 7 are graphs illustrating a difference of blood measurement time delay according to blood flow and heart rate according to an embodiment.

Figure 6A:
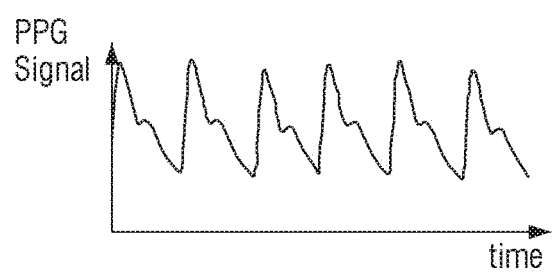
FIGS. 6A, 6B, 7A and 7B are graphs illustrating a difference of blood measurement time delay according to blood flow and heart rate according to an embodiment.
Figure 6B:
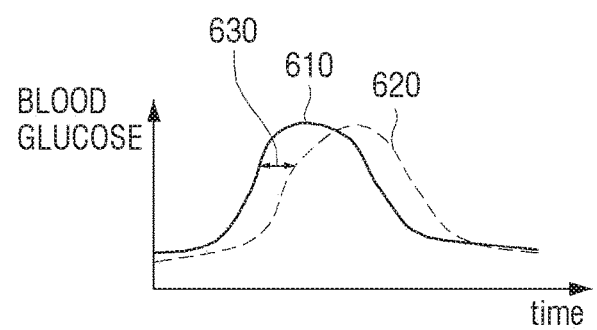

FIGS. 6A and 6B are a graph illustrating the PPG signal according to time when the blood flow in the blood vessel is relatively low or heart rate is low. FIG. 6B is a graph illustrating a time delay 630 between an actual blood glucose 610 and blood glucose 620 of the interstitial fluid measured by the first sensor of the electronic device 100 in accordance with times.

Figure 7A:
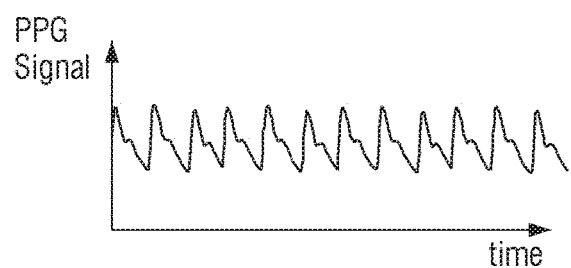
Figure 7B:
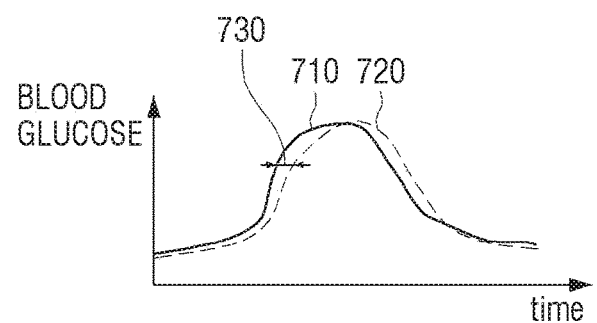

FIGS. 7A and 7B are a graph illustrating the PPG signal according to time when the blood flow in the blood vessel is relatively high or heart rate is high. FIG. 7B is a graph illustrating a time delay 740 between an actual blood glucose 710 and blood glucose 720 of the interstitial fluid measured by the first sensor of the electronic device 100 in accordance with times.

Referring to FIGS. 6 and 7, according to one embodiment, the electronic device 100 may determine the blood flow and/or heart rate based on the characteristics of the signal such as the amplitude of the signal generated by the PPG sensor and the distance of the peak, or the like, and advance the measurement time of the glucose of the interstitial fluid when blood flow and/or heart rate is high. Accordingly, it can be known that glucose 720 of the interstitial fluid measured when the blood flow and/or heart rate is high may have a value substantially similar to the value of glucose 710 in actual blood. Therefore, according to one embodiment of the disclosure, the electronic device 100 may have an effect to significantly reduce an error in prediction of blood glucose, which is caused by the time delay of glucose diffusion from the glucose in the blood into the glucose of the interstitial fluid, using the PPG sensor.

FIGS. 8 and 9 are views to describe a skin contact state of the electronic device according to an embodiment.

Referring to FIGS. 8 and 9, the electronic device 100 may include the first sensor 110 inserted into the skin and the second sensor 120 in contact with the surface of the skin. The second sensor 120 may be composed of the LED and the PD. The second sensor 120 may detect light which is not absorbed by the blood and tissues and reflected on the skin through the PD. Therefore, the electronic device 100 may determine the state in which the first sensor 110 is inserted into the human body and the state in which the second sensor 120 is in contact with the skin based on the signal generated by the PD.

Figure 8A:
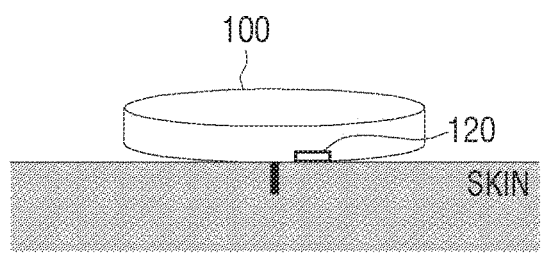
FIGS. 8A, 8B, 9A and 9B are views to describe a skin contact state of the electronic device according to an embodiment.
Figure 8B:
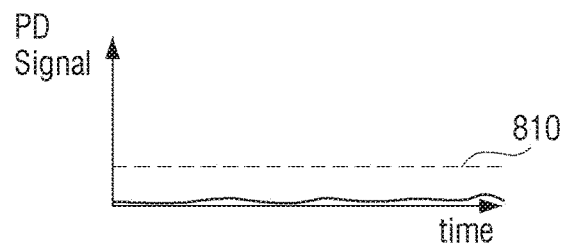

FIGS. 8A and 8B are a view illustrating that the electronic device 100 is completely in contact with the skin. Referring to FIG. 8A, the first sensor 110 is inserted into the human body, and the surface of the second sensor 120 is completely in contact with the skin. Therefore, the PD of the second sensor 120 may detect the amount of light reflected from the skin to be small. For example, referring to FIG. 8B, the PD signal of the second sensor 120 may be kept constant at a threshold 810 or below.

Figure 9A:
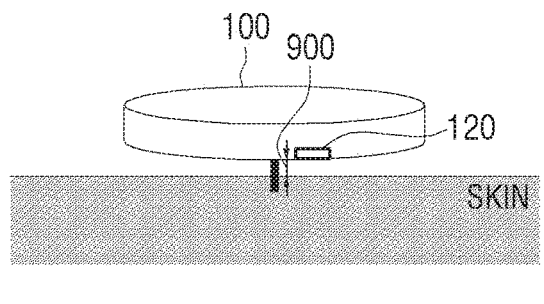
Figure 9B:
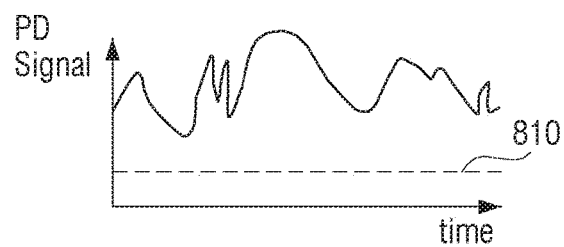

FIGS. 9A and 9B are a view illustrating a state in which the electronic device 100 is apart from the skin by a predetermined space 900. Referring to FIG. 9A, it may be seen that a part of the first sensor 110 is inserted to the human body, and a part of the sensor is out of the skin. In addition, it may be seen that the surface of the second sensor 120 is not in contact with the skin.

When the signal generated by the PD of the second sensor 120 has a variable value at the threshold value or above, the electronic device 100 may determine that the first sensor 110 is not inserted into the human body and provide a connection failure warning to the user.

For example, referring to FIG. 9B, the PD signal of the second sensor 120 may have a variable value at a threshold value 810 or above. That is, the PD of the second sensor 120 may sense the light reflected from the skin and the light introduced from the outside through a space 900 which is apart from the skin. Accordingly, the signal generated by the PD of the second sensor 120 may be varied at the threshold 810 or above by the detection of ambient light.

The electronic device 100 may measure the blood glucose of a diabetes patient in real time and provide the patient with the data and thus, if the first sensor 110 is not completely inserted into the skin, accurate blood glucose may not be measured. Therefore, when the signal generated by the PD of the second sensor 120 is variable in the threshold or above, the electronic device 100 may provide the user with a warning that the first sensor 110 is not inserted into the human body.

The electronic device 100 may implement a warning in various ways. That is, the warning notification may be a warning sound, a warning text, vibration, or the like, but is not limited thereto. In addition, the electronic device 100 may provide the warning notification to other electronic devices which communicate with the electronic device 100.

FIGS. 10 and 11 are views to describe hypoglycemia detection algorithm according to an embodiment.

Figure 10A:
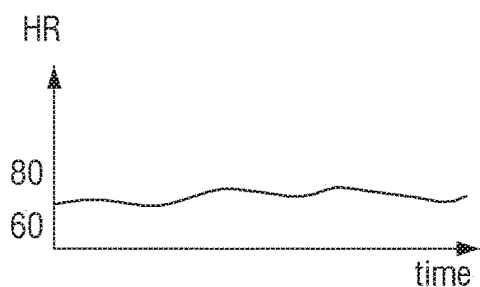
FIGS. 10A, 10B, 11A and 11B are views to describe hypoglycemia detection algorithm according to an embodiment.
Figure 10B:
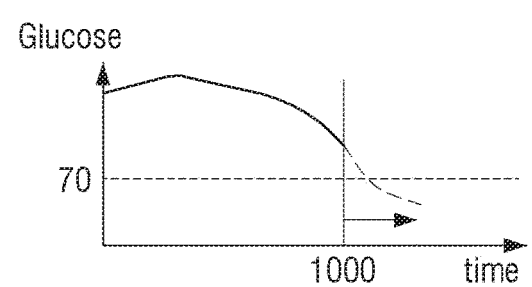

FIGS. 10A and 10B are a view to describe a hypoglycemic prediction notification when the heart rate is in a normal range.

Referring to FIG. 10A, if the heart rate measured by the second sensor of the electronic device 100 is shown to be constant between 60 and 80 over time, the heart rate may be in the normal range. The electronic device 100 may predict a hypoglycemic point 1000 by analyzing the slope and pattern of the graph indicating the glucose level of the interstitial fluid. Referring to FIG. 10B, if the heart rate is within the normal range, the electronic device 100 may provide the hypoglycemic prediction warning at the specific time 1000 when the level of the glucose in the interstitial level falls to the threshold value or below.

Figure 11A:
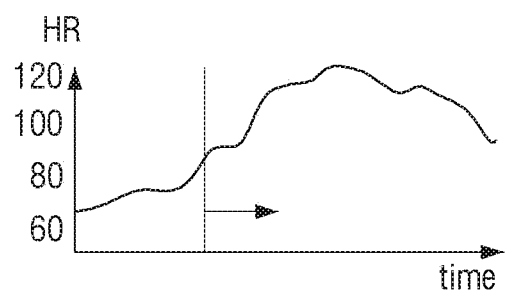
Figure 11B:
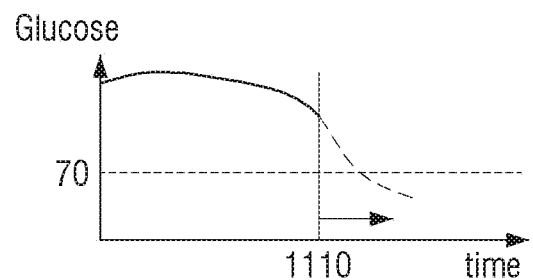

FIGS. 11A and 11B are a view to describe a hypoglycemic prediction notification when the heart rate is out of a normal range.

Referring to FIG. 11A, a heart rate measured by the second sensor of the electronic device 100 may have a sudden rise at the arbitrary time 1110. At this time, when the heart rate measured by the second sensor is equal to or higher than the designated value, in order to advance the hypoglycemic prediction time, the electronic device 100 may set the slope value at the point where the glucose level of the interstitial fluid measured by the first sensor becomes a designated value or less to be greater than or equal to the threshold value.

For example, referring to FIG. 11B, it may be predicted that the level of glucose of the interstitial fluid measured by the first sensor may suddenly fall at the time 1110 when the heart rate suddenly increased, and the slope value of the graph of the glucose level at the time 1110 may be set to be equal to or higher than the threshold value. Therefore, the electronic device 100 may provide the hypoglycemic notification more rapidly, in comparison with the normal heart rate (FIG. 10B).

Figure 12:
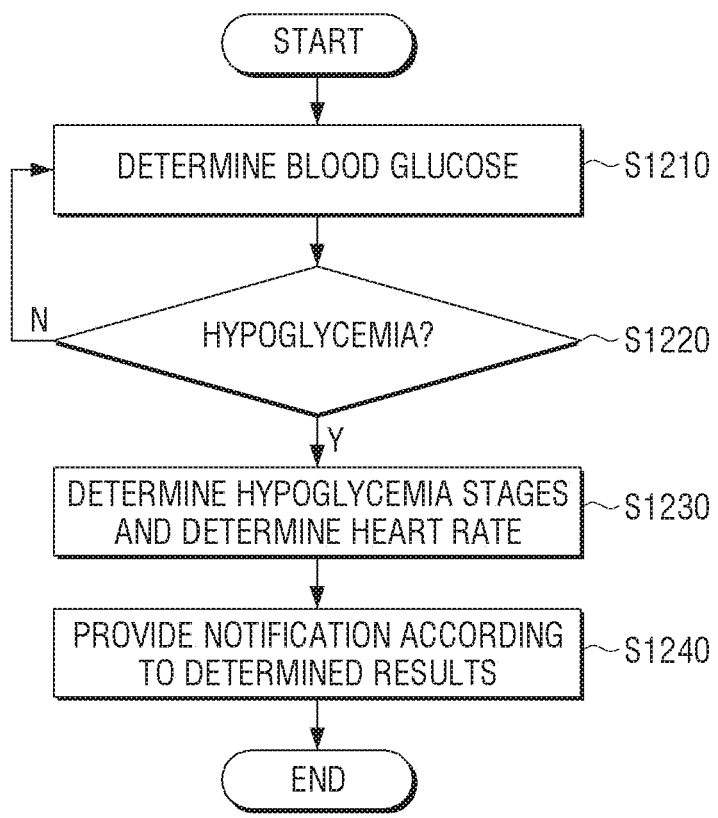
FIG. 12 is a flowchart to describe a method for providing a hypoglycemia warning notification based on the heart rate according to an embodiment.

FIG. 12 is a flowchart to describe a method for providing a hypoglycemia warning notification based on the heart rate according to an embodiment.

Referring to FIG. 12, in step S1210, the electronic device 100 may determine the blood glucose value based on the glucose of the interstitial fluid measured by the first sensor and the blood flow and/or heart rate data measured by the second sensor.

In step S1220, the electronic device 100 may determine hypoglycemia according to the blood glucose value.

When the blood glucose value is included in the range of hypoglycemia in step S1220-Y, the electronic device 100 may determine the hypoglycemic stage including the blood glucose value in step S1230. In addition, the electronic device 100 may determine the heart rate measured by the second sensor by stages according to the heart rates.

For example, the value of a blood glucose entering hypoglycemia may be 70 mg/dl. In addition, the first stage of hypoglycemia is a stage where dizziness may be felt, and the blood glucose value may be 50 to 70 mg/dl. The second stage of hypoglycemia is a stage where dizziness may be felt, and heart is rapidly beating, and the blood glucose value may be 30-50 mg/dl. The third stage of hypoglycemia is a stage in which a person may lose consciousness and fall down, and the blood glucose value may be 30 mg/dl or less, and the heart rate may fall off suddenly to the designated value or below. The above-described example is only one example for describing the disclosure, but is not limited thereto.

In step S1240, the electronic device 100 may provide different warning notifications according to the determined hypoglycemia stages.

The electronic device 100 may predict the glucose level to be measured later, on the basis of the level of the glucose level measured by the first sensor and store the predicted glucose level in the storage. In addition, when the glucose level predicted at a specific time zone is equal to or less than a designated value, the electronic device 100 may provide the user with the hypoglycemic notification prior to the specific time zone.

For example, when the blood glucose value is predicted to be 70 mg/dl at the specific time, the electronic device 100 may provide the hypoglycemic notification prior to the actual measurement of the blood glucose value to be 70 mg/dl, and five to 30 minutes earlier than the specific time.

In the case of the second stage of hypoglycemia, the electronic device 100 may provide the hypoglycemia notification to external electronic devices communicating with the electronic devices 100 or emergency contacts stored in the electronic device 100 to seek help.

In the case of the third stage of hypoglycemia, the electronic device 100 may provide the hypoglycemic notification and the position information of the electronic device 100 to the electronic device 100 and the emergency rescue center (for example, medical staff, hospitals, 911 Center, or the like).

The electronic device 100 may include various information such as a current position of the electronic device 100, blood glucose level, a list of foods for supplementing glucose, heart rate, or the like, as the hypoglycemic notification information.

According to another embodiment of the disclosure, as described above in FIG. 1, the electronic device 100 may include the first sensor for measuring the blood glucose, and the external electronic device 300 may include the second sensor for measuring the heart rate and/or blood flow. At this time, the electronic device 100 may determine the blood glucose based on the heart rate sensing data received from the external electronic device 300, and may provide the determined blood glucose information to the external electronic device 300. The external electronic device 300 may provide various notifications to the user based on the blood glucose information received from the electronic device 100.

For example, the external electronic device 300 may be a wearable device such as a smart watch, but is not limited thereto. The smart watch may provide the user with warning notifications which are different by stages of the hypoglycemia based on the hypoglycemia stage information received from the electronic device 100.

For example, the smart watch may provide warning notification of hypoglycemia by stages as text messages and/or vibrations. In addition, the smart watch may provide the user with golden time information in differentiated colors by stages of hypoglycemia. The smart watch may provide the user with notification by stages of hypoglycemia with a warning sound and/or a text message as a sound. For example, when the first stage of the hypoglycemia warning is entered, the sound warning such as "You are in the first stage of hypoglycemia and need to eat sweet food" may be provided.

Figure 13:
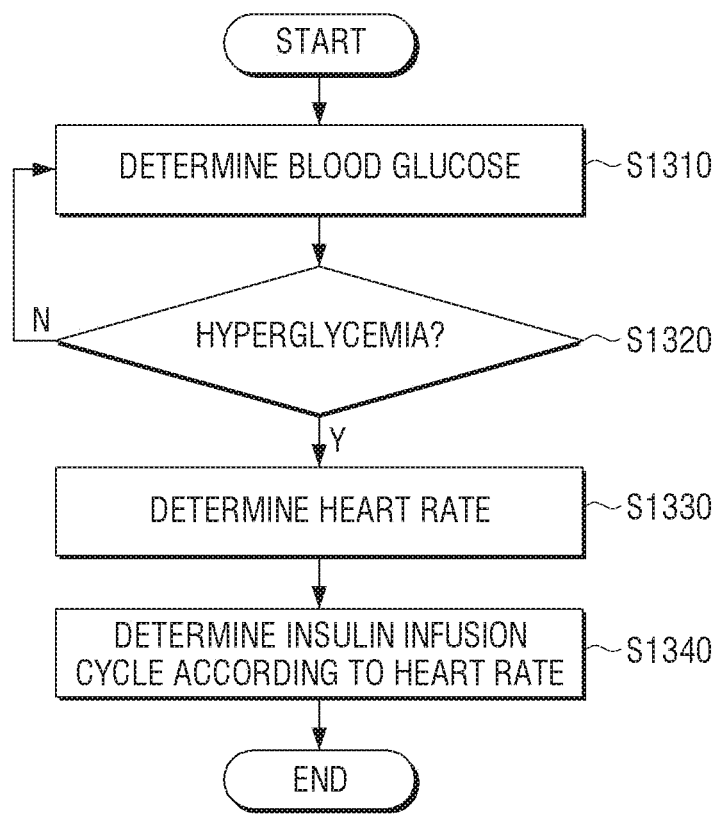
FIG. 13 is a flowchart to describe a method for determining an insulin infusion cycle to a hyperglycemic patient based on heart rate according to an embodiment.

FIG. 13 is a flowchart to describe a method for determining an insulin infusion cycle to a hyperglycemic patient based on heart rate according to an embodiment.

The electronic device 100 may include an insulin pump for a patient with hyperglycemia. In addition, when the insulin pump is not included, the electronic device 100 may control the external electronic device by setting insulin infusion cycle of the insulin pump to the external electronic device including the insulin pump, based on the blood glucose and the heart rate information measured by the electronic device 100.

Referring to FIG. 13, in step S1310, the electronic device 100 may determine blood glucose. This has been described in step S1210 of FIG. 12 and will not be further described.

In step S1320, the electronic device 100 may determine hyperglycemia.

When the predicted blood glucose value is included in the range of the hyperglycemia in step S1320-Y, the electronic device 100 may determine the heart rate through the second sensor and store the heart rate in the storage in step S1330.

In step S1340, the electronic device 100 may determine the insulin infusion cycle according to the heart rate.

For example, when the heart rate is rapid to be 120 or higher, if the insulin is infused into the human body, the insulin may rapidly spread and thus, the electronic device 100 may check the blood glucose every ten minutes and re-determine the amount of insulin infusion.

In addition, when the heart rate is between 60 and 120, which is the normal range, the electronic device 100 may determine the insulin infusion cycle based on the time cycle applied by an ordinary CGM device. For example, the electronic device 100 may check blood glucose every 20 minutes and re-determine the insulin infusion amount.

In addition, when the heart rate is slow to be 60 or below, the electronic device 100 may consider that the insulin spreads in the body slowly, and re-determine the insulin infusion amount by checking the blood glucose every 30 minutes.

The range of heart rate and insulin cycle time described above are merely one embodiment and are not limited thereto.

Figure 14:
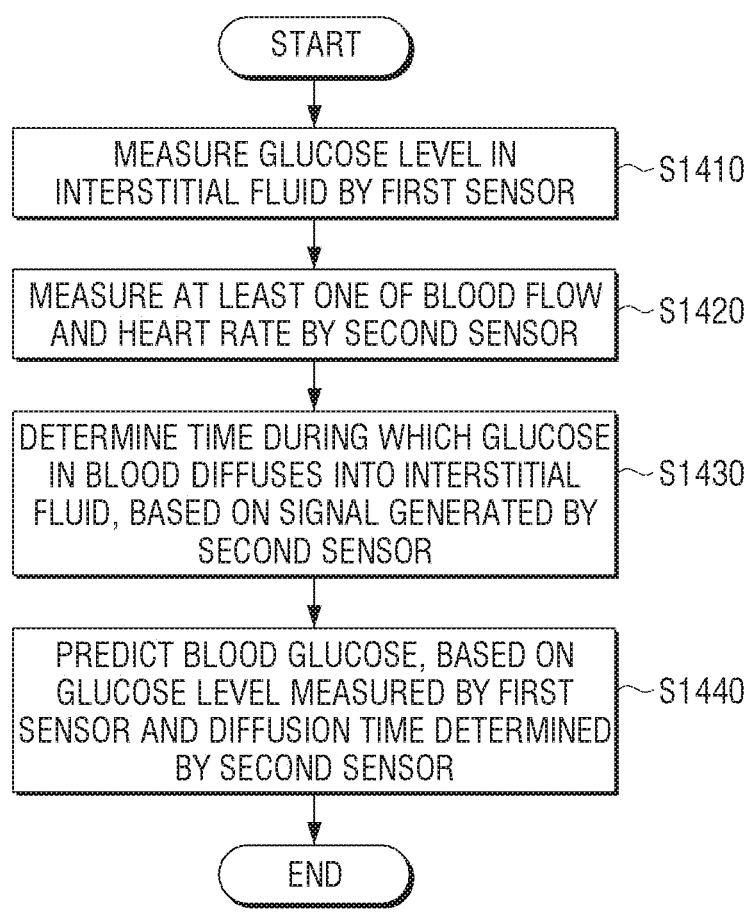
FIG. 14 is a view to describe a method for providing a continuous glucose monitoring according to an embodiment.

FIG. 14 is a view to describe a method for providing a continuous glucose monitoring according to an embodiment.

Referring to FIG. 14, in step S1410, the electronic device 100 may measure the glucose level of the interstitial fluid by the first sensor. The first sensor may be a glucose sensor used in an electronic device providing the CGM.

In step S1420, the electronic device 100 may measure at least one of blood flow and/or heart rate of a human body by the second sensor. The second sensor may be the PPG sensor or an electrocardiogram sensor capable of measuring the heart rate, but is not limited thereto.

In step S1430, the electronic device 100 may determine the time when glucose in the blood diffuses into the interstitial fluid based on the signal generated by the second sensor.

In step S1440, the electronic device 100 may predict the blood glucose in the blood based on the glucose level measured by the first sensor and the glucose diffusion time of the interstitial fluid determined by the second sensor.

The methods according to embodiments of the disclosure may be implemented in the form of program instructions that may be executed through various computer means and recorded on a computer readable medium. The computer readable medium may include program instructions, data files, data structures, etc., alone or in combination. For example, the computer-readable medium may be stored, whether removable or rewritable, in a volatile or non-volatile storage device, such as a storage device such as a ROM, or a memory such as a RAM, a memory chip, a device, or an integrated circuit, or a storage medium readable by a machine (e.g., a computer) as well as being optically or magnetically recordable, such as, for example, a CD, DVD, magnetic disk or magnetic tape.

It will be appreciated that the memory that may be included in the electronic device is one example of a machine-readable storage medium suitable for storing programs or programs including instructions for implementing the embodiments. Program instructions to be recorded on the storage medium may be those specially designed and constructed for the disclosure or may be available to those skilled in the art of computer software.

As described above, although the present disclosure has been described with reference to the embodiments and the accompanying drawings, it is to be understood that the present disclosure is not limited thereto, and various variations and modifications may be made by those skilled in the art without departing from the spirit and scope of the present disclosure as defined by the appended claims.

Therefore, the scope of the disclosure should not be limited to the embodiments described, but should be determined by equivalents to the claims, as well as the claims to be described later.

What is claimed is:

1. An electronic device for providing continuous blood glucose monitoring, the electronic device comprising:
   a first sensor for measuring a glucose level of an interstitial fluid in order to predict a blood glucose;
   a second sensor disposed on an inner surface of the electronic device configured to be in contact with a human body, in order to measure at least one of a blood flow or a heart rate of the human body; and
   a processor configured to:

based on a height of an amplitude of a signal in an alternating current (AC) portion, where a signal change is present, is less than or equal to a designated value periodically:
    determine that at least one of the blood flow or the heart rate are out of a normal range,
    determine a diffusion time to be proportional to the heart rate, and
    predict the blood glucose based on the glucose level measured by the first sensor and the determined diffusion time.

2. The electronic device of claim 1, wherein the processor is further configured to, based on a peak-to-peak interval of the signal being less than or equal to the designated value:
    determine that at least one of the blood flow or the heart rate are out of the normal range,
    determine the diffusion time to be proportional to at least one of the blood flow and the heart rate.

3. The electronic device of claim 1, wherein the processor is further configured to, based on a size of a direct current (DC) value in a DC portion, where the signal change is not present, is-being less than or equal to the designated value:
    determine that at least one of the blood flow or the heart rate are out of the normal range,
    determine the diffusion time to be proportional to at least one of the blood flow and the heart rate.

4. The electronic device of claim 1,
wherein the second sensor comprises a photo diode (PD), and
wherein the processor is further configured to determine whether the first sensor is inserted into the human body according to a signal generated by the PD.

5. The electronic device of claim 4, wherein the processor is further configured to, based on the signal generated by the PD having a variable value at a threshold value or higher:
    determine that the first sensor is not inserted into the human body, and
    provide a user with a connection failure warning.

6. The electronic device of claim 1, wherein the processor is further configured to, based on at least one of the heart rate or the blood flow generated by the signal being greater than or equal to a designated value, control the first sensor by setting a slope value of a point at which the glucose level measured by the first sensor is less than or equal to a designated value to be greater than or equal to a threshold value to advance hypoglycemic prediction time.

7. The electronic device of claim 1, wherein the processor is further configured to:
    predict a glucose level to be measured based on a level of the glucose measured by the first sensor by times, and
    provide a user with a hypoglycemic notification prior to a time when the predicted glucose level is less than or equal to a designated value.

8. The electronic device of claim 7, wherein the processor is further configured to, based on at least one of the blood flow the heart rate being greater than or equal to threshold values, and the measured glucose level being within a designated range, provide the hypoglycemic notification.

9. The electronic device of claim 1, further comprising:
an insulin pump,
wherein the processor is further configured to, based on the predicted blood glucose indicating hyperglycemia, determine an insulin infusion cycle differently by times based on at least one of the blood flow or the heart rate.

10. A method for providing continuous blood glucose monitoring by an electronic device, the method comprising:
    measuring a glucose level of an interstitial fluid in order to predict blood glucose by a first sensor;
    measuring at least one of a blood flow or a heart rate of a human body by a second sensor disposed on an inner surface of the electronic device configured to be in contact with the human body;
    based on a height of an amplitude of a signal in an alternating current (AC) portion, where a signal change is present, being less than or equal to a designated value, periodically:
        determining that at least one of the blood flow or the heart rate are out of a normal range;
        determining a diffusion time to be proportional to the heart rate; and
    predicting the blood glucose based on the glucose level measured by the first sensor and the determined diffusion time.

11. The method of claim 10, wherein the determining of the diffusion time comprises, based on a peak-to-peak interval of the signal being less than or equal to the designated value:
    determining that at least one of the blood flow or the heart rate are out of the normal range, and
    determining the diffusion time to be proportional to at least one of the blood flow or the heart rate.

12. The method of claim 10, wherein the determining of the diffusion time comprises, based on a size of a direct current (DC) value in a DC portion, where the signal change is not present, being less than or equal to the designated value:
    determining that at least one of the blood flow or the heart rate are out of the normal range, and
    determining the diffusion time to be proportional to at least one of the blood flow or the heart rate.

13. The method of claim 10,
wherein the second sensor comprises a photo diode, and
the method further comprising determining whether the first sensor is inserted into the human body according to a signal generated by the photo diode.

* * * * *